United States Patent [19]

Galetto et al.

[11] Patent Number: 5,165,291
[45] Date of Patent: Nov. 24, 1992

[54] METHOD AND APPARATUS FOR MEASURING THE FLOW

[75] Inventors: William G. Galetto, Baldwin, Md.; Laura K. Kent-Riggs, Coppell, Tex.

[73] Assignee: McCormick and Company, Inc., Hunt Valley, Md.

[21] Appl. No.: 698,192

[22] Filed: May 6, 1991

Related U.S. Application Data

[63] Continuation of Ser. No. 482,844, Feb. 22, 1990, abandoned.

[51] Int. Cl.$^5$ ............................................. G01N 19/00
[52] U.S. Cl. ..................................................... 73/866
[58] Field of Search ............... 73/866, 863.52, 863.81, 73/863.86; 222/565, 480-482, 485, 486, 548, 142.9

[56] References Cited

U.S. PATENT DOCUMENTS

| | | | |
|---|---|---|---|
| 646,846 | 4/1900 | Lepore | 222/142.9 |
| 725,638 | 4/1903 | Thurston | 222/142.9 |
| 960,650 | 6/1910 | Lind | 222/142.9 |
| 1,198,395 | 9/1916 | Marshall . | |
| 1,291,371 | 1/1919 | Bell . | |
| 1,437,345 | 11/1922 | Marr | 222/142.9 |
| 1,579,892 | 4/1926 | Shaw | 222/142.9 |
| 1,602,745 | 10/1926 | Binkele | 222/142.9 |
| 1,863,291 | 6/1932 | Weston . | |
| 2,264,223 | 11/1941 | Stancliffe . | |
| 2,633,027 | 3/1953 | Bunnell . | |
| 3,122,925 | 3/1964 | Kregel . | |
| 3,221,560 | 12/1965 | Kosa et al. . | |
| 3,376,753 | 4/1968 | Pitkin . | |
| 3,439,841 | 4/1969 | Rhodes | 222/142.9 |
| 3,521,750 | 7/1970 | Hamilton . | |
| 3,636,772 | 1/1972 | Bennett . | |
| 3,665,768 | 5/1972 | Hosokawa et al. . | |
| 3,693,458 | 9/1972 | Odell . | |
| 3,940,997 | 3/1976 | Hudson . | |
| 4,079,621 | 3/1978 | Batzar . | |
| 4,181,023 | 1/1980 | Clamroth et al. . | |
| 4,274,286 | 6/1981 | Gioia . | |
| 4,320,657 | 3/1982 | Johnson, III . | |
| 4,586,386 | 5/1986 | Hollstein et al. . | |

FOREIGN PATENT DOCUMENTS 0648871 2/1979 U.S.S.R. ............................. 73/863.86

OTHER PUBLICATIONS

Grover Scientific Inc. (brochure).

*Primary Examiner*—Robert Raevis
*Attorney, Agent, or Firm*—Oblon, Spivak, McClelland, Maier & Neustadt

[57] ABSTRACT

A flow machine for measuring the flowability of granular or powered material. A container for receiving the material to be measured is provided with a rotatable disc assembly which selectively opens and closes apertures defined through the transverse wall of the material container. Further, a collection container is mountable to the material container for receiving material which passes through the apertures in the transverse wall of the material container. In order to measure the flow rate of a material placed within the material container, the rotatable disc assembly is rotated to close the apertures of the material container, and a material to be tested is placed within the container. The rotatable disc assembly is then rotated to open the apertures in the base of the material container and the material container with collection container coupled thereto is rotated. Once the rotation has been completed the rotatable disc assembly is again rotated to close the apertures of the material container and the material which was has passed into the collection container is measured to determine the flowability of the material.

11 Claims, 3 Drawing Sheets

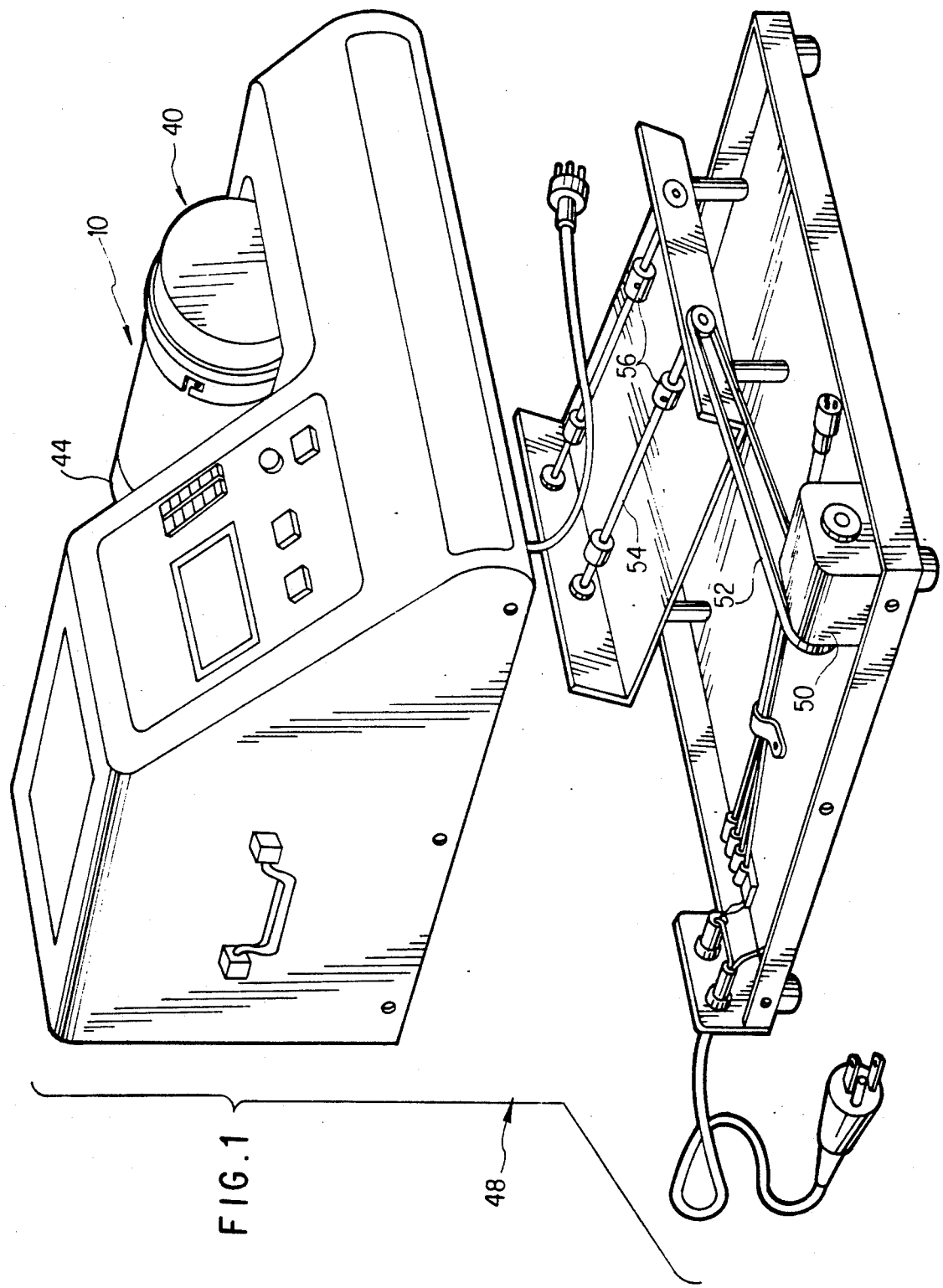

METHOD AND APPARATUS FOR MEASURING THE FLOW

This is a continuation of application Ser. No. 07/482,844, filed on Feb. 22, 1990, which was abandoned upon the filing hereof continuation Ser. No. 698,192.

BACKGROUND OF THE INVENTION

Field of the Invention

The present invention relates to a method and apparatus for measuring the flowability of powdered or granular materials.

The measurement of the fluid characteristics of powdered or granular materials is a critical factor in planning and designing dispensing devices for such materials in the food processing industry and in the processing of pharmaceuticals. Indeed, in many manufacturing processes it is necessary to convey predetermined amounts of granular or powder material from a supply hopper to a blending or packaging apparatus. With such manufacturing processes, it is critical that a predetermined amount of the material be accurately dispensed and that sequential batches have identical compositions. In order for an accurate and reproducible amount of material to be conveyed from the hopper, the precise flowability of the material within the hopper must be uniform and controlable.

An example of a prior art flow meter is the Photron Flowable Solids Quantifier available from Grover Scientific, Inc. of Saratoga, Calif. The Photron device includes a screen through which the material to be tested passes and elements for agitating the material so it will flow to and through the screen. The agitating elements are spring biased and are actuated by a trigger assembly which is operated by a technician. Because the Photron has a number of moving parts and must be continuously actuated by a technician, and because flow through the screen cannot be selectively prevented, accurate and reproducible results are difficult to obtain.

While a variety of methods for testing the flowability of materials have been developed, presently there is no known satisfactory method for measuring the relative flowability of powdered materials in a manner which is both reproducible and accurate. As noted above, however, there is a need for such a reliable method of determining the flowability of materials having different physical characteristics as well as the flow of a particular material under varying physical conditions. Indeed, the particle shape, size and size distribution of the material will influence the flow rate of a particular material. Furthermore, varying physical conditions such as temperature, moisture content and the like will influence the flow rate of a particular material.

It would therefore be desirable to provide a simple, accurate and reproducible measuring device which enables the quick and easy determination of the flowability of materials such as seasonings and pharmaceuticals.

SUMMARY OF THE INVENTION

It is an object of the present invention to provide a method and apparatus for measuring the flow rate of powdered and granular materials which is precise, does not exhibit significant unit to unit variations, is durable, yields consistent results from operator to operator, is easy to clean, and relatively inexpensive.

These and other objects are achieved in accordance with the present invention by placing the material to be tested in a cylindrical container having a number of fairly large apertures defined in the bottom surface thereof and a lid which closes the top of the cylinder. A disc shaped closure device is mounted within the cylindrical container for closing the apertures prior to testing. A secondary collection container, slightly larger than the cylindrical container, is attached to the base of the cylindrical container to receive material passing through the bottom apertures. The cylinder containing the material and with the secondary container attached thereto is placed in a horizontal position, the apertures are opened and the cylinder is rotated about a horizontal axis passing through its center. After a predetermined period of rotating the container, or a predetermined number of rotations, the apertures defined in the base of the cylindrical container are closed and the material received in the secondary container is weighed to determine the flowability of the material being tested.

Other objects, features and characteristics of the present invention, as well as the methods of operation and functions of the related elements of the structure, and the combination of parts and economies of manufacture, will become more apparent upon consideration of the following detailed description and the appended claims with reference to the accompanying drawings all of which form a part of this specification, wherein like reference numerals designate corresponding parts in the various figures.

BRIEF DESCRIPTION OF THE DRAWINGS

FIG. 1 is an exploded perspective view showing a solids flow monitoring device formed in accordance with the present invention;

DESCRIPTION OF THE PRESENTLY PREFERRED EXEMPLARY EMBODIMENT

The present invention is directed to a method and apparatus for measuring a flow rate of a powdered material by imparting energy to the material to be measured or to the surface or surfaces over which the material is passed while the flow rate is being measured. It has been found that by imparting such energy, the measurement can be obtained in a reduced period of time and with increased accuracy.

Figure 2:
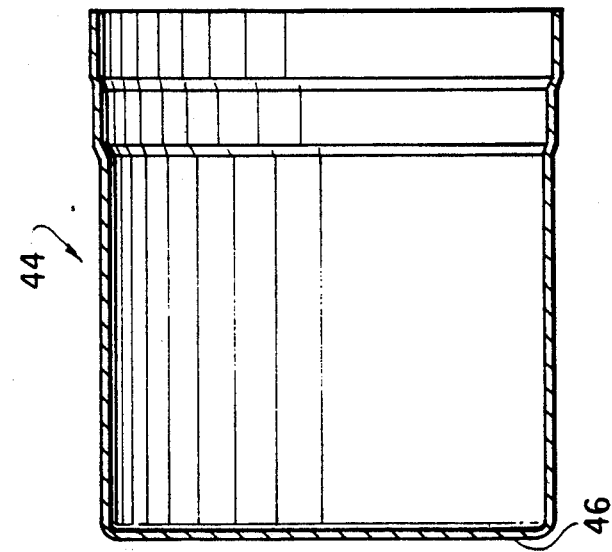
FIG. 2 is an exploded view, partly in section, of a testing cylinder formed in accordance with the present invention.

Referring to FIG. 2, the container 10 for the material to be tested formed in accordance with the present invention includes a main chamber 12 having a cylindrical sidewall 14 and a flat bottom wall 16. A plurality of apertures 18 are defined through the bottom wall 16 and are preferably substantially larger than the particles of material to be tested so that a sifting, sorting or grading of the material does not occur. For example, the apertures 18 are preferably on the order of 50 to 100 times larger than the particle size of the material being tested. While in the illustrated embodiment, a bottom wall of the container is provided which has apertures defined therethrough, it is to be understood that an apertured transverse wall could be provided at a particular location along the longitudinal axis thereof, the container having an open bottom end.

Figure 3:
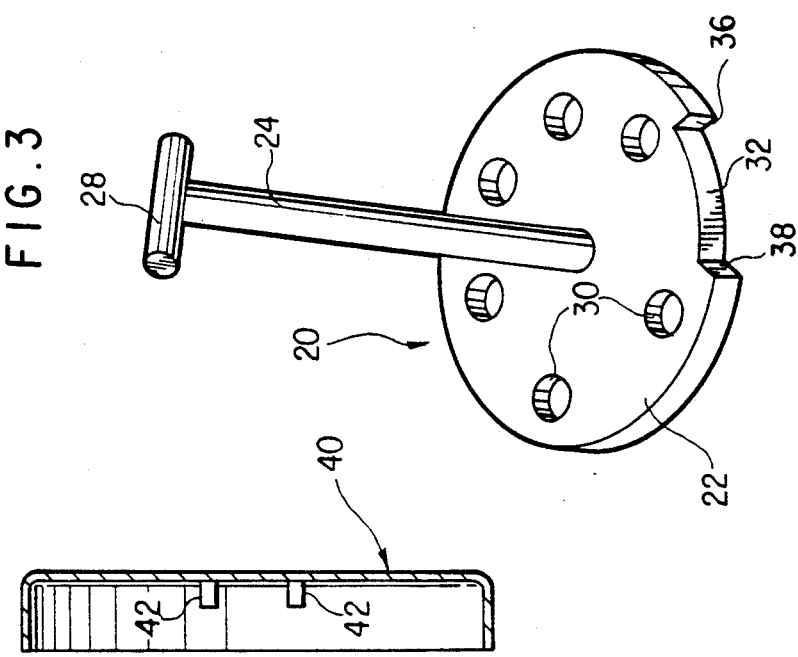
FIG. 3 is a schematic perspective view of a disc closure assembly for the testing cylinder formed in accordance with the invention.

Mounted within the main cylindrical chamber 12 is a disc closure assembly 20 which can be seen most clearly in FIG. 3. The disc closure assembly 20 is mounted so that the disc 22 is disposed interiorly of the cylindrical container 10 adjacent bottom 16. The disc 22 itself is fixedly mounted to a shaft 24 which is disposed centrally of the cylindrical container 10 and extends through an aperture 26 defined in the bottom wall 16 of container 10 so as to be rotatable relative thereto while preventing the passage of the material to be measured through the coupling. The opposite end of the shaft 24 is provided with a knob 28 or the like which, when rotated, will effect rotation of the disc 22 within the cylindrical container 10.

Figure 4:
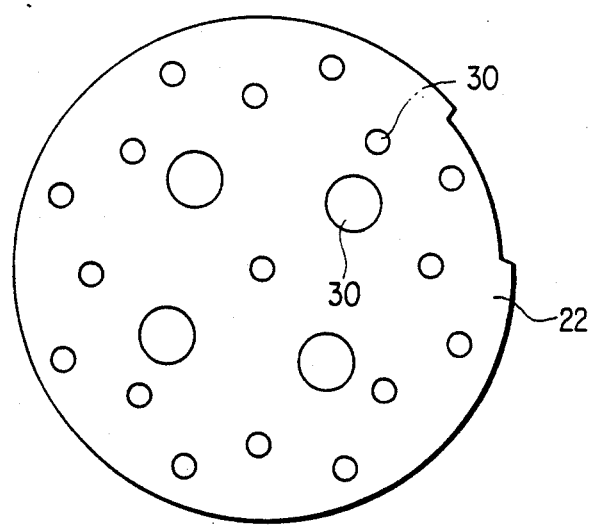
FIG. 4 is a top plan view of a disc closure showing one of the possible configurations of holes therein.

The disc 22 has a plurality of apertures 30 which are disposed so as to correspond to some or all locations of the apertures 18 in the bottom 16 of cylindrical container 10. Further, the apertures of disc 22 and of bottom wall 16 are disposed such that in one position the apertures of the disc and at least some of the apertures of the bottom wall will be aligned and in a second position, angularly displaced from the first position, the apertures 30 of the disc 22 will be offset from all of the apertures 18 of the bottom wall 16 and thus the disc 22 closes off the apertures 18 of the cylindrical container 10. One possible configuration of apertures 30 is shown, for example, in FIG. 4. It is to be understood in this regard that while the apertures 30 of the disc and the apertures 18 of bottom wall 16 could be disposed to define only two positions, one with all apertures in facing relation to, that is coincident, and thus fully opened and one with all apertures offset and thus fully closed, alternative aperture configurations could be provided having more than just two positions. For example, an alternative configuration could be provided wherein additional positions are available so that, referring to FIG. 4, only the large apertures or only the small apertures are in registration with apertures in the bottom wall. In this way, the number and size of openings could be varied to adjust for the particular powder materials that are being quantified.

As can be seen in FIG. 3, a slot 32 is preferably defined along the circumferential edge of the disc element 50 and slidably receives an index pin 34 (FIG. 2) extending through the bottom 16 and into the interior 12 of the cylindrical container 10. Thus, rotation of knob 28 of shaft 24 in a clockwise direction will cause rotation of the disc until the index pin 34 engages one end 36 of the slot 32 in the disc 22 and prevents further rotation thereof. In this second position the disc 22 has been rotated so as to fully close the apertures 18 in the bottom of the cylindrical container 10.

The lid 40 for the cylindrical container 10 has first and second knob engaging lugs 42 defined on the interior surface thereof. Thus, when the lid 40 is mounted to the cylindrical container 10, as discussed more fully below, secure engagement of the lid 40 of the cylindrical container 10 will cause engagement of the lugs 42 with the knob 28 on the end of the shaft 24. Rotation of the lid 40 relative to the cylindrical container 10, then, will rotate the knob 28 and in turn rotate the disc 22 coupled to this shaft 24. Where more than simply open and closed positions are provided, indicia can be provided on the lid and/or container so that a particular flow configuration can be selected.

A collection container 44 is further provided and is sized so that its open end can be received over the bottom end of the cylindrical container 10. The opposite end 46 of the collection container 44 is closed so that material passing from the main material chamber 12 through apertures 18 defined in the bottom thereof and into the collection container 44 will be held in the collection container 44 until removal is desired. The collection container 44 can be slidably coupled to the main container 10 and frictionally retained thereon or screw threads can be defined on the respective containers for screw threaded coupling of the containers. Other coupling structures could of course be provided though not shown in particular.

In order to test the flowability of a particular granular or powdered material, the main cylindrical container 10 with disc 22 and shaft 24 mounted thereto are engaged with the collection container 44. The knob 28 on the shaft 24 is then rotated in a clockwise direction to the second position so as to displace the apertures 30 in disc 22 from the apertures 18 in the base of cylindrical container 10 and thus close the base of the container. A predetermined amount of powder or granular material to be measured, such as 500 grams of seasoning, are then added to the interior of the cylinder. The lid 40 is attached to the open end of the cylinder 10 and turned clockwise until the lid lugs 42 engage the knob 28 on the end of the shaft 24. The assembled cylindrical canister is turned to a horizontal position and placed in the agitation machine 48 shown in FIG. 1.

As is shown schematically is FIG. 1, agitation machine 48 incldues a motor 50 which rotates a drive belt 52 engaged with first and second shafts 54 having driving cams 56 mounted thereon. Thus, when the motor 50 is activated the drive belt 52 will rotate the shafts 54 and frictional engagement between the cams 56 and the cylindrical wall 14 of the container 10 cause rotation of the cylinder within the agitation machine 48.

In order to allow material to flow from the bottom surface 16 of the cylinder 10, the lid 40 is turned in a counterclockwise direction immediately prior to activation of the motor 48, which in turn rotates the knob 28 of the shaft 24 and hence the disc 22 in a counterclockwise direction until the pin stop 34 engages the opposite end 38 of the slot 32, Thus the apertures 30 of the disc 22 are coincident with the apertures 18 in the base 16 of the cylinder. The machine 48 is then started and the cylinder 10 rotated as discussed above.

Once the cylinder 10 has been rotated for a predetermined period or a predetermined number of revolutions, the machine 48 is stopped and the lid 40 is turned in a clockwise direction to again close the holes 18 of the cylinder. Engagement of the pin stop 34 with end 36 of the slot 32 defines this second, closed position of the disc closure assembly. The material container 10 is then removed from machine 48 and placed in an upright position. The collection container 44 is separated from the bottom of the cylinder and the material therein is weighed to record the amount of material flowed from the cylinder during the operation of the machine.

Figure 5:
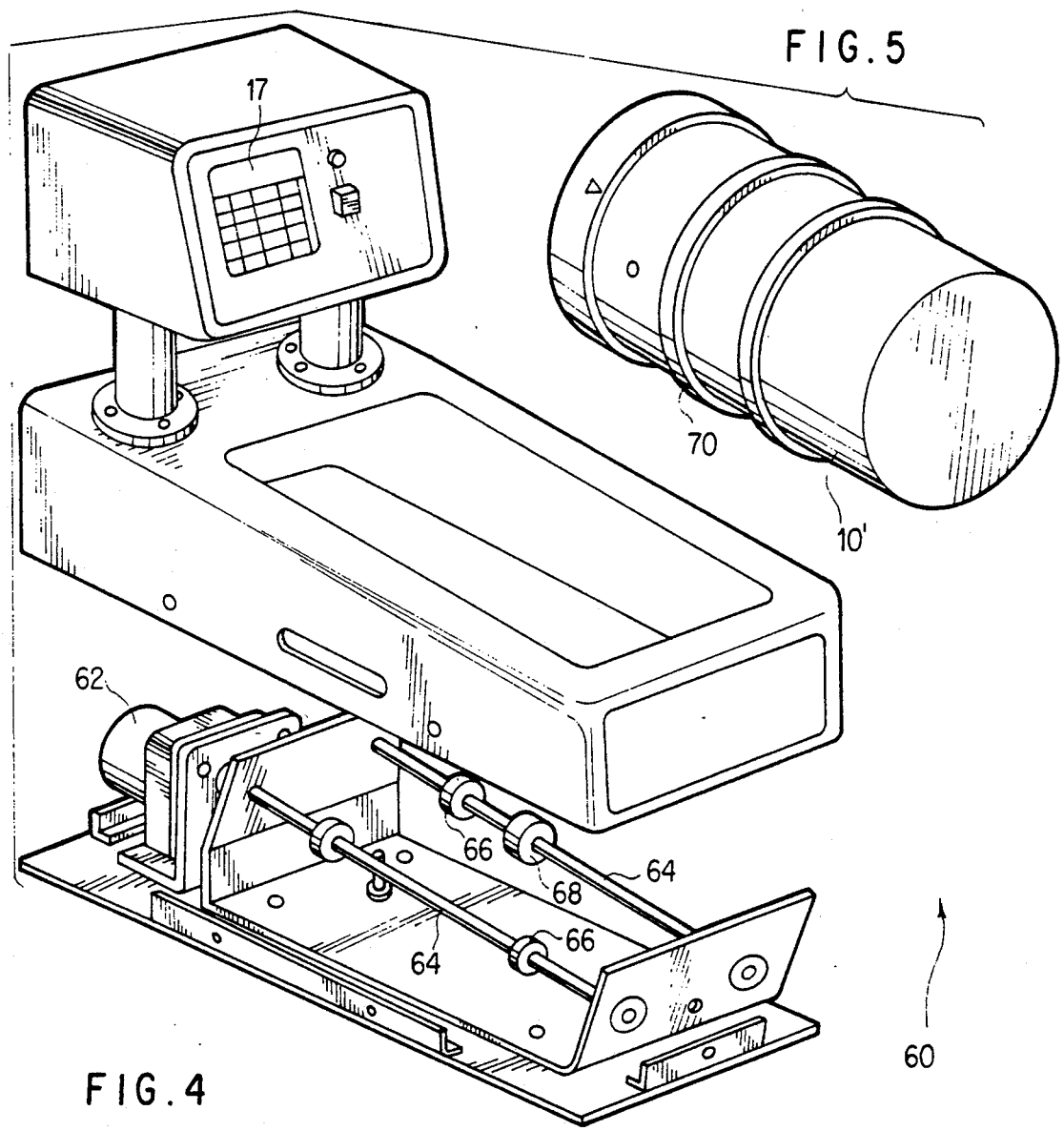
FIG. 5 is an exploded perspective view showing an alternate solids flow monitoring device formed in accordance with the present invention.

An alternate agitation machine 60 is shown in FIG. 5. As can be seen, this embodiment is more compact than machine 48 and thus takes up less bench space. Agitation machine 60 has a motor 62 operatively engaged with at least one of shafts 64, each of which has driving cams 66 mounted thereon. Further, in this embodiment, at least one of the shafts has a toothed wheel 68 which engages a corresponding track 70 defined on cylinder 10' to ensure that cylinder 10' will rotate as shafts 64 rotate so that an accurate flow measurement can be made.

As is apparent from the foregoing, because the apertures of the disc of the are alignable with the openings in the cylinder and the disc is provided interiorally of the cylinder, a worker can more easily handle the container without loosing any of the powdered material contained therewithin. Furthermore, the provision of a closed collector rigidly coupled to the main cylinder ensures that all the flowed material is collected and reserved until final measurement.

The advantageous and distinguishing features of the apparatus and method of the invention can be more fully appreciated upon a review of the comparative data presented below wherein the invention (McFlow Quantifier) was compared to the Photron Quantifier, briefly discussed above.

| TECHNICIAN VARIABILITY STUDY | | |
| --- | --- | --- |
| | McFlow | Photron |
| | Standard Deviation | |
| Instrument 1 | 19.1 | 35.0 |
| Instrument 2 | 10.5 | 47.0 |
| Instrument 3 | 11.5 | 59.4 |
| Instrument 4 | 11.8 | 45.6 |
| | Ranges | |
| Overall Range | 48 grams | 133 grams |
| Average Range | 28 grams | 97 grams |

| INSTRUMENT VARIABILITY STUDY | | |
| --- | --- | --- |
| | Range Between Instrument Means | |
| | McFlow | Photron |
| Nacho (4 instr. × 4 days) | 55 grams | 115 grams |
| Italian Cheese and Herb (3 instr. × 2 days) | 3 grams | 88 grams |
| Nacho (adjusted low flow) (3 instr. × 2 days) | 3 grams | 25 grams |
| BBQ (4 instr. × 3 days) | 26 grams | 69 grams |

As discussed above, the Photron has a number of moving parts and is actuated by hand. As a result, reproducibility between units and from test to test is a problem. The device of the invention, on the other hand, has only a few simple parts. As demonstrated above, then, the invention exhibits superior reproducibility between units as compared to the prior art Photron device.

While the invention has been described in connection with what is presently considered to be the most practical and preferred embodiment, it is to be understood that the invention is not limited to the disclosed embodiment, but, on the contrary, it is intended to cover various modifications and equivalent arrangements included within the spirit and scope of the appended claims. For example, because certain powders may build up static electricity within the container that affects the powders' actions and hence the results of the measurements, it is to be appreciated that the device could be grounded in any suitable manner to ensure accurate measurements.

What is claimed is:

1. An apparatus for measuring the flowability of powered or granular material comprising:
   a material container including side walls, a transverse wall, and an open upper end, said transverse wall having a plurality of apertures defined therethrough said transverse wall having an inner surface and an outer surface, said inner surface facing an interior of said container and said open upper end;
   a rotatable disc closure assembly mounted to said container, said rotatable disc assembly including a disc mounted immediately adjacent to said transverse wall and having a plurality of apertures defined therethrough so that when said disc is in a first position at least some of the apertures of said disc are coincident with at least some of the apertures of said transverse wall and so that when said disc is rotated to a second position, angularly displaced from said first position, the apertures of said disc are offset from the apertures of said transverse wall so that said disc closes the apertures of said transverse wall, and a longitudinal shaft fixedly coupled at one end thereof to said disc for rotating said disc relative to the transverse wall of said container so that rotation of the longitudinal shaft about the longitudinal axis thereof rotates said disc; the other end of said shaft extending towards said open upper end of said container; and
   a collection container removably coupleable to said material container so as to be in facing relation to said outer surface of said transverse wall so as to receive material which passes through the apertures of said transverse wall from the interior of the material container.

2. An apparatus as in claim 1, further comprising a lid element for closing said open end of said material container.

3. An apparatus as in claim 2, wherein said lid element includes means for engaging the other end of said shaft so that rotation of said lid rotates said shaft.

4. An apparatus as in claim 1, wherein said disc element includes a slot-like cutout portion and wherein a pin stop element extends through the transverse wall of said material container so as to be slideably disposed within said slot whereby engagement of first and second ends of said slot with said pin stop element limits rotation of said disc relative to said transverse wall.

5. An apparatus as in claim 4, wherein engagement of said pin stop element with one end of said slot defines said second position wherein said disc closes off the apertures of said transverse wall and engagement of said pin stop element with another end of said slot defines said first position wherein the apertures of said disc are aligned with the apertures of said transverse wall.

6. An apparatus as in claim 1, wherein said transverse wall is a bottom wall of the material container.

7. An apparatus for measuring the flowability of powered or granular material comprising:
   a material container including side walls, a transverse wall, and an open upper end, said transverse wall having a plurality of apertures defined therethrough;
   a rotatable disc closure assembly mounted to said container, said rotatable disc assembly including a disc mounted immediately adjacent to said transverse wall and having a plurality of apertures defined therethrough so that when said disc is in a first position at least some of the apertures of said disc are coincident with at least some of the apertures of said transverse wall and so that when said disc is rotated to a second position, angularly displaced from said first position, the apertures of said disc are offset from the apertures of said transverse wall so that said disc closes the apertures of said transverse wall, and a longitudinal shaft fixedly coupled at one end thereof to said disc for rotating said disc relative to the transverse wall of said container, the other end of said longitudinal shaft extending toward said open upper end of said container;

a lid element for closing said open upper end of said material container, said lid element including means for engaging the upper end of said shaft so that rotation of said lid rotates said shaft.

8. An apparatus for measuring the flowability of powdered or granular material comprising:

a material container having side walls, first and second longitudinal ends, and a transverse wall, said transverse wall having a plurality of apertures defined therethrough;

a rotatable disc closure assembly mounted to said container, said rotatable disc assembly including a disc mounted immediately adjacent to said transverse wall and having a plurality of apertures defined therethrough so that when said disc is in a first position at least some of the apertures of said disc are coincident with at least some of the apertures of said transverse wall and so that when said disc is rotated to a second position, angularly displaced from said first position, the apertures of said disc are offset from the apertures of said transverse wall so that said disc closes the apertures of said transverse wall, and a longitudinal shaft fixedly coupled at one end thereof to said disc for rotating said disc relative to the transverse wall of said container, the other end of said shaft extending toward one of said ends of said container;

a first closure element removably coupleable to said first end of said container; and a second closure element removably coupleable to the second end of said container.

9. An apparatus as in claim 8, wherein said longitudinal shaft is mounted to said disc so that rotation of the longitudinal shaft about the longitudinal axis thereof rotates said disc.

10. An apparatus as in claim 8, wherein said transverse wall is defined at said second end of the material container and wherein said second closure element defines a collection container removably coupleable to said material container to receive material which passes through the apertures of said transverse wall.

11. An apparatus as in claim 8, wherein the other end of said shaft extends toward the first end of said container and said first closure element includes means for engaging the other end of said shaft so that rotation of said first closure element moves said longitudinal shaft to thereby move said disc relative to the transverse wall of said container.

* * * * *